United States Patent [19]
Zetter et al.

[11] Patent Number: 5,663,071
[45] Date of Patent: Sep. 2, 1997

[54] HUMAN THYMOSIN β 15 GENE, PROTEIN AND USES THEREOF

[75] Inventors: Bruce R. Zetter, W. Newton; Lere Bao, Brookline, both of Mass.

[73] Assignee: Children's Medical Center Corporation, Boston, Mass.

[21] Appl. No.: 664,856

[22] Filed: Jun. 17, 1996

[51] Int. Cl.$^6$ .......................... C07H 21/02; C07H 21/04; C12N 5/00; C12N 15/00
[52] U.S. Cl. ...................... 435/325; 536/23.1; 536/23.5; 435/320.1; 435/358; 435/365; 435/367
[58] Field of Search .................... 536/23.1, 23.5; 514/44; 530/300; 436/94; 435/69.1, 71.1, 240.2, 320.1

[56] References Cited

PUBLICATIONS

Montell et al., The drosophila ninaC locus encodes two photoreceptor cell specific proteins with domains homologous to protein kinases and the myosin heavy chain head, Cell, vol. 52, pp. 757–772 Mar. 1988.
Rudin et al., Differential splicing of thymosin β–4 mRNA, J. Immunol., vol. 144(12), pp. 4857–4862 Jun. 1990.
Hiller et al., The WashU–Merck EST project, EST–STS, accession #R08518 Apr. 1995.
Nachmiar, V., Current Opinion in Cell Biology, 1993, 5:56.
Safer, et al., Proc. Natl. Acad. USA 1990 87:2536–2540.
Safter, et al., J. Biol. Chem., 1991, 268:4029–4032).
D. Safer, J. Muscle Res. Cell Motil, 1992, 13:269–271).
Weber, et al., Biochemistry 1992, 31:6179–6185).
Yu, et al., J. Biol. Chem., 1993, 268:502–509.
Cassimeris, et al., J. Cell Biol., 1992, 119:1261–1270.
Low, et al., Arch. Biochem. Biophys., 1992, 293:32–39.
Low, et al., Proc. Natl. Acad. Sci., USA 1981, 78:1162–1166.
Rebar, et al., Science 1981, 214:669–671.
Gomez–Marquez, et al., J. Immunol. 1989, 143:2740–2744.
Bao, et al., The American Association for Cancer Research annual meeting (Mar.18–22, 1995), Abstract.
Clauss, et al., Genomies 1991, 9:75–180.
Sanders, et al., Proc. Natl. Acad. Sci. USA 1992, 89:4678–4682.

Primary Examiner—George C. Elliott
Assistant Examiner—Andrew Wang
Attorney, Agent, or Firm—David G. Conlin; David S. Resnick; Dike, Bronstein, Roberts & Cushman

[57] ABSTRACT

The present inventors have now discovered that humans have a gene that encodes a novel protein of the thymosin β family. This novel protein, herein referred to as thymosin β15, has the ability to bind and sequester G-actin, like other members of the thymosin β family, but unlike what is known about other members it also directly regulates cell motility in prostatic carcinoma cells. The present invention is directed to an isolated cDNA encoding the human thymosin β15 gene (SEQ ID NO: 1) and have deduced the amino acid sequence (SEQ ID NO: 2).

10 Claims, 7 Drawing Sheets

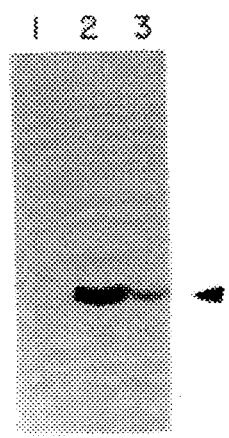
FIG.1A
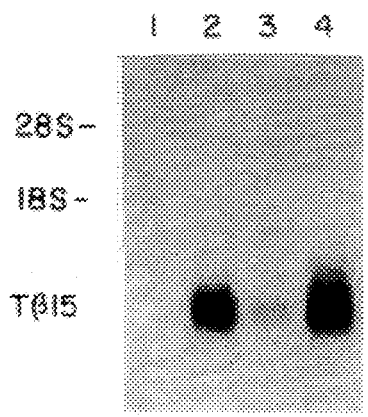
FIG.1B
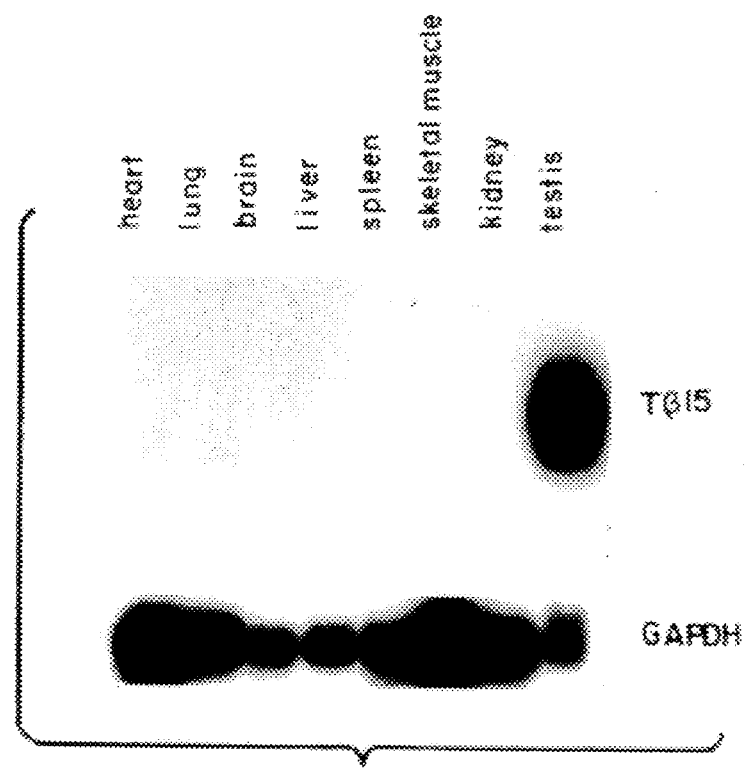
FIG.4

FIG. 2

```
TATCAGCTAG TGGCTGCACC CGGAACACC  ACCCTGGTCC GGAGTAGCTG CGGACAGAAT      60

TGCTGGCCTA GTAGAAGCTT TGGAACGAGC AGTCAAG ATG AGT GAT AAA CCA GAC     115
                                          M   S   D   K   P   D

TTA TCA GAA GTT GAA ACA TTT GAC AAA TCA AAG TTG AAG AAG ACT AAT      163
 L   S   E   V   E   T   F   D   K   S   K   L   K   K   T   N
 1

ACT GAA GAA AAG AAT ACT CTT CCT TCG AAG GAA ACT ATC CAG CAG GAG      211
 T   E   E   K   N   T   L   P   S   K   E   T   I   Q   Q   E

AAA GAA TAT AAT CAA AGA TC ATAAAATGAG ATTCTCCCTCT CAAGAGCAAC TTCAAC  267
 K   E   Y   N   Q   R   S   *

TTTGCTGGAT AGTCTTGGAT TTAGACATGT TTCTGTAAAC CTATCCAATA TGTAGACATT    327
TTAGGCGGTT CCTGATAGGT TCTTAAGTAC CCTGACTGAA AGGTCAGCAT TTAACACCAA    387
TCATTAAATG TGTTTTCCAC TGCTC                                          412
```

FIG. 3

| | | | | |
|---|---|---|---|---|
| Ratthymb4    | .MSDKPDMAE | IEKFDKSKLE | KTETQEKNPL | PSKETIEQEK | QAGES..... | 49 |
| Bovthymb9    | AQADKPDLGE | INSFDKAKLE | KTETQEKNTL | PTKETIEQEK | QAK....... | 50 |
| Ratthymb10   | .MADKPDMGE | IASFDKAKLE | KTETQEKNTL | PTKETIEQEE | RSETS..... | 49 |
| Troutthymb11 | ACSDKPNLEE | VASFDKITKLE | KTETQEKNPI | PTKETIEQEE | QAS....... | 50 |
| Troutthymb12 | ACSDKPDLAE | VSNFDKITKLE | KTETQEKNPL | PTKETIEQEE | QAT....... | 50 |
| Humanthymb15 | .MSDKPDLSE | VETFDKSKLE | KINIEEKNTL | PSKETIQQEK | EYNQRS.... | 49 |

HUMAN THYMOSIN β 15 GENE, PROTEIN AND USES THEREOF

The work described herein was supported, in part, by National Institutes of Health grant CA37393. The U.S. Government has certain rights to this invention.

BACKGROUND OF THE INVENTION

The present invention provides novel genes, proteins, and uses thereof including, methods for diagnosing and treating cancer, particularly metastatic cancer.

Most eukaryotic cells (execptions include red blood cells and adult muscles) contain high concentrations, i.e., up to ~250 μmol/l, of momomeric actin. How such actin remains unpolymerized in the cytoplasm has remained a problem in cell biology (Nachmiar, V., *Current Opinion in Cell Biology*, 1993, 5:56). Profilin, originally thought to be the actin-sequestering protein, is not present in sufficient amounts to account for more than part of the monomeric actin levels observed. Recently, an actin-sequestering 5 kD peptide was discovered in high concentration in human platelets (Safer, et al., *Proc. Natl. Acad. Sci* U.S.A. 1990 87:2536–2540) and shown to be identical to a previously known peptide (Safter, et al., *J. Biol. Chem.*, 1991, 268:4029–4032) originally thought to be the thymic hormone, thymosin $\beta_4$ (T$\beta_4$) (D. Safer, *J. Muscle Res. Cell Motil*, 1992. 13:269–271). A detailed kinetic study of the interaction of T$\beta_4$ and actin (Weber, et al., *Biochemistry* 1992, 31:6179–6185)), together with other studies (Yu, et al., *J. Biol. Chem.*, 1993, 268:502–509 and Cassimelds, et al., *J. Cell Biol.*, 1992, 119:1261–1270) support the hypothesis that T$\beta_4$ and T$\beta_{10}$ function primary as G-actin buffers. Unpublished data (E. Hannappel) extend the function to several other β thymosins. T$\beta_4$ has also been shown to inhibit nucleotide exchange by actin, whereas profilin increases the rate of exchange (Coldschmidt-Clermont, et al., *Mol. Cell Biol.*, 1992, 3:1015–1025).

All vertebrates studied contain one or often two β-thymosins. Thus, the members of the β-thymosin family are believed to be important in all species. Three new family members (Low, et al., *Arch. Biochem. Biophys.*, 1992, 293:32–39 and Schmid, B., Ph.D Thesis, University of Tubingen 1989) have been found in perch, trout and in sea urchin, the first non-vertebrate source. The sequences are well conserved suggesting that actin sequestration is probably a property of all β-thymosins. However, when T$\beta_4$ was discovered and its sequence first determined in 1981 (Low, et al., *Proc. Natl. Acad. Sci.*, U.S.A. 1981, 78:1162–1166), data were presented that suggested two extracellular functions (Low, et al. supra and Rebar, et al., *Science* 1981, 214:669–671). Two recent papers indicate a different and unexpected effect of a tetrapeptide which may be derived from the amino terminus of T$\beta_4$.

Several reports demonstrate regulation of T$\beta_4$ or T$\beta_{10}$ synthesis at the transcriptional or translational level. An interferon-inducible gene (Cassimelds, et al., *J. Cell. Biol.* 1992, 119:1261–1270 and Sanders, et al., *Proc. Natl. Acad. Sci.* U.S.A. 1992, 89:4678–4682) is identical to the cDNA of human T$\beta_4$, and there are several genes for T$\beta_4$ in humans. (Clauss, et al., *Genomies* 1991, 9:75–180 and Gomez-Marquez, et al., *J. Immunol.* 1989, 143:2740–2744)

It would be desirable to identify new members of the β-thymosin family, particularly in humans.

Bao and Zetter reported in an abstract presented at the American Association for Cancer Research annual meeting (Mar. 18–22, 1995) the differential expression of a novel mRNA expressed in high-metastatic rat tumor cell lines, but not in a low metastatic variant. cDNA was isolated and was reported to encode a protein with 68% identity to the rat thymosin $\beta_4$. However, the nucleotide sequence and the deduced amino acid sequence were not reported.

SUMMARY OF THE INVENTION

We have now discovered that humans have a gene that encodes a novel protein of the thymosin β family. This novel protein, herein referred to as thymosin β15, has the ability to bind and sequester G-actin, like other members of the thymosin β family, but unlike what is known about other members it also directly regulates cell motility in prostatic carcinoma cells. We have isolated a cDNA of the human thymosin β15 gene (SEQ ID NO: 1) and have deduced the amino acid sequence (SEQ ID NO: 2). We have shown that enhanced transcripts (mRNA) and expression of the thymosin β15 gene in non-testicular cells has a high correlation to disease state in a number of cancers, such as prostate, lung, melanoma and breast cancer, particularly metastatic cancers. Accordingly, discovering enhanced levels of transcript or gene product in non-testicular tissues can be used in not only a diagnostic manner, but a prognostic manner for particular cancers.

The present invention provides isolated nucleic acids (polynucleotides) which encode thymosin β15 having the deduced amino acid sequence of SEQ ID. NO: 2 or a unique fragment thereof. The term "unique fragment" refers to a portion of the nucleotide sequence or polypeptide of the invention that will contain sequences (either nucleotides or amino acid residues) present in thymosin β15 (SEQ ID NO: 2) but not in other member of the thymosin family. This can be determined when the hybridization profile of that fragment under stringent conditions is such that it does not hybridize to other members of the thymosin family. Such fragments can be ascertained from FIG. 3. A preferred set of unique fragments are those that contain, or contain polynucleotides that encode, amino acid 7 to 12 of SEQ ID NO: 2, amino acid 21 to 24 of SEQ ID NO: 2 and amino acid 36 to 45 of SEQ ID NO: 2. Preferably, the unique nucleotide sequence fragment is 10 to 60 nucleotides in length, more preferably, 20 to 50 nucleotides, most preferably, 30 to 50 nucleotides. Preferably, the unique polypeptide sequence fragment is 4 to 20 amino acids in length, more preferably, 6 to 15 amino acids, most preferably, 6 to 10 amino acids.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in SEQ ID NO: 1 or may be a different coding sequence which coding sequence, as a result of the redundancy or degeneracy of the genetic code, encodes the same protein as the DNA of SEQ ID NO: 1.

The polynucleotide may have a coding sequence which is a naturally occurring allelic variant of the coding sequence shown in SEQ ID NO: 1. As known in the art, an allelic variant is an alternate form of a polynucleotide sequence which may have a substitution, deletion or addition of one or more nucleotides, which does not substantially alter the function of the encoded protein.

The present invention also provides an isolated polynucleotide segment which hybridize under stringent conditions to a unique portion of the hereinabove-described polynucleotides, particularly SEQ ID NO: 1. The segment preferably comprises at least 10 nucleotides. As herein used, the term "stringent conditions" means hybridization will occur only if there is at least 95% and preferably at least 97% identity between the sequences. These isolated segments may be used in nucleic acid amplification techniques, e.g., PCR, to identify and/or isolate polynucleotides encoding thymosin β15.

As used herein a polynucleotide "substantially identical" to SEQ ID NO:1 is one comprising at least 90% homology, preferably at least 95% homology, most preferably 99% homology to SEQ ID NO: 1. The reason for this is that such a sequence can encode thymosin β15 in multiple mammalian species.

The present invention further provides an isolated and purified human thymosin β15 having the amino acid sequence of SEQ ID NO: 2, or a unique fragment thereof, as well as polypeptides comprising such unique fragments, including, for example, amino acid 7 to 12 of SEQ ID NO: 2, amino acid 21 to 24 of SEQ ID NO: 2 and amino acid 36 to 45 of SEQ ID NO: 2.

In accordance with yet another aspect of the present invention, there are provided isolated antibodies or antibody fragments which selectively binds human thymosin β15. The antibody fragments include, for example, Fab, Fab', F(ab')2 or Fv fragments. The antibody may be a single chain antibody, a humanized antibody or a chimeric antibody.

The term "isolated" means that the material is removed from its original environment (e.g., the natural environment if it is naturally occurring). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

The present invention further provides a method of treating a neoplastic cell expressing human thymosin β15 by administering to the cell an effective amount of a compound which suppresses the activity or production of the human thymosin β15. Preferably, the compound interferes with the expression of the human thymosin β15 gene. Such compounds include, for example, antisense oligonucleotides, ribozymes, antibodies, including single chain antibodies and fragments thereof.

DESCRIPTION OF THE DRAWINGS

FIGS. 1A and 1B show differential mRNA display and Northern analysis of Dunning R-3327 rat prostatic adenocarcinoma variants. Total RNA from AT2.1 (lane 1), AT3.1 (lane 2) and AT6.1 (lane 3) cells were reverse-transcribed and amplified by PCR with a primer set, $T_{11}$ AG and a 10 mer AGGGAACGAG (SEQ ID NO:3) in the presence of [α35-S]dATP. The PCR fragments were displayed on a 6% polyacrylamide gel and autoradiographed. The differentially expressed band is indicated by arrowhead. B. Northern blot analysis of thymosin β15 gene. Two μg of poly (A) RNA was isolated from Dunning R-3327 variants AT2. I (lane 1), AT3.1 (lane 2), AT6.1 (lane 3), and Mat Lylu (lane 4), fractionated on a 1.1% formaldehyde-agarose gel, transferred to Hybond-N+ nylon membrane (Amersham) and hybridized with a random primed (Grillon C, et al., FEBS 1990, 274:30–34) $^{32}$P-labeled Tβ15 cDNA fragment. The same blot was hybridized with a rat β-actin probe to demonstrate that equivalent amounts of RNA were loaded in each lane.

FIG. 2 is the nucleotide sequence (SEQ ID NO.: 1) of Tβ15 cDNA and the predicted amino acid sequence (SEQ ID NO.: 2) (single-letter code). The sequence numbers of the nucleotides and amino acids are indicated on the right side of the sequences. The translation initiation codon ATG is underlined, and the termination codon TAA is marked with an asterisk. A putative actin binding region is underlined. These sequence data are available from GenBank under accession number U25684.

FIG. 3 shows the alignment of the deduced Tβ15 protein sequence and some of the other β thymosin isoforms. Regions of amino acid identity are represented by white letters boxed in black. Unboxed black letters correspond to nonidentical regions. Dots correspond to gaps introduced in the sequence to optimize alignment.

FIG. 4 shows expression of Tβ15 in various rat tissues. The multiple-tissue blot was obtained from Clontech. The blot was hybridized with the Tβ15 cDNA probe. Rat GAPDH is a loading control.

FIG. 5A shows differential expression in tumors. The small arrow shows positive staining. The large arrow shows negative staining. FIG. 5B shows that in poorly differentiated and invasive prostate carcinoma, single cell invading stroma display intense staining (arrow).

FIG. 6A. 3 μM of pyrene-labeled G-actin was polymerized in the presence of various amounts of GST-Tβ4 fusion peptide (▼), GST-Tβ15 (▲) or GST alone (○). The final extent of polymerization was determined from the final levels of pyrene-labeled actin (fluorescence). All solutions contained 5.5 mM Tris, pH7.6, 167 μM $CaCl_2$, 0.5 mM glutathione, 167 μM DTT, and 420 μM ATP. Polymerization was induced by addition of 2 mM $MgCl_2$ and 150 mM KCl. Error bars denote the range of duplicate measurements made from separate dilutions of the fusion proteins.

FIG. 6B. 2 μM of pyrene-labeled G-actin was polymerized in the presence of various amounts of monomeric Tβ15 that had been cleaved from GST by thrombin. The relative rates of polymerization were derived from the maximal rate of fluorescence increase in the initial phase of polymerization.

FIG. 6C. The final extent of actin assembly was determined by the same methods used for the thymosin GST fusion peptides. Experimental conditions are those described for FIG. 6B.

FIG. 7A. Vector control transfected (○, ▽) and Tβ15 antisense (●, ▼) transfected AT3.1 cell clones. FIG. 7B. Vector control transfected (○, ▽) and Tβ15 sense transfected (●, ▼) AT2.1 cell clones. Data are expressed as the mean ±SE (n=4). FIG. 7C. Growth curves of control transfected and Tβ15 (sense or antisense) transfected Dunning R-3327 clones. Cells from vector control transfected AT2.1 (○), Tβ15 sense transfected AT2.1 (●), vector control transfected AT3.1 (▽) and Tβ15 antisense transfected AT3.1 (▼) were plated at initial $10^4$ cells/well in RPMI 1640 with 10% FBS and 250 nM dexamethasome in 12-well plates. Cells were harvested and counted at indicated times. Points represent the mean ±SE (n=3).

FIG. 8A is a Coomasie staining of GST-Tβ fusion proteins. FIG. 8B is a Western analysis of GST-Tβ fusion proteins with affinity purified anti-Tβ15 C-terminal peptide antibody. Lane 1: GST-Tβ4; Lane 2: GST-Tβ15; Lane 3: GST only

DETAILED DESCRIPTION OF THE INVENTION

Figure 5A:
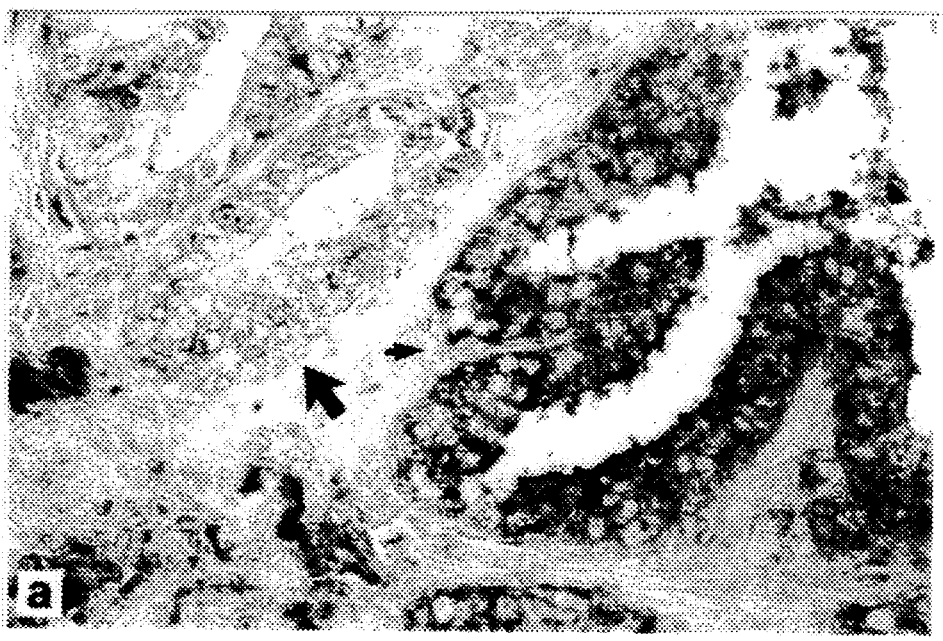
FIGS. 5A and 5B show in situ hybridization with antisense riboprobe for Tβ15 on prostatic adenocarcinoma patients.

A well characterized series of cell lines that show varying metastatic potential has been developed from the Dunning rat prostatic carcinoma (Isaacs, et al., *Prostate* 9, 261–281 and Bussebakers, et al., *Cancer Res.* 52,2916–2922 (1992)). Coffey and colleagues previously showed a direct correlation between cell motility and metastatic potential in the Dunning cell lines (Mohler, et al., *Cancer Res.* 48, 4312–4317 (1988), Parin, et al., *Proc. Natl. Acad. Sci,* U.S.A. 86, 1254–1258 (1989) and Mohler, et al., *Cancer Metast. Rev* 12, 53–67 (1993)). We compared gene expression in poorly metastatic and highly metastatic cell lines derived from Dunning rat prostate carcinoma using differential mRNA display. The results of these studies revealed the expression of a novel member of the thymosin beta family of actin-binding molecules, thymosin β15. Using this information, we isolated and sequenced a cDNA encoding human thymosin β15.

Although members of the thymosin β family have been shown to bind and sequester G-actin, they have not previously been demonstrated to alter cell motility. Our studies, however, reveal that this new member, thymosin β15, directly regulates cell motility in prostatic carcinoma cells. We have shown that expression of thymosin β15 is upregulated in highly metastatic prostate cancer cell lines relative to poorly metastatic or nonmetastatic lines. In addition, thymosin β15 was expressed in human prostate carcinoma specimens but not in normal human prostate. Although not wishing to be bound by theory, this indicates that β15 plays a role in the process of metastatic transformation.

The present invention provides a polynucleotide sequence encoding all or part of thymosin β15 having the deduced amino acid sequence of SEQ ID NO:2 or a unique fragment thereof. A nucleotide sequence encoding human thymosin β15 is set forth as SEQ ID NO: 1.

The sequences of the invention may also be engineered to provide restriction sites, if desired. This can be done so as not to interfere with the peptide sequence of the encoded thymosin β15, or may interfere to any extent desired or necessary, provided that the final product has the properties desired.

Where it is desired to express thymosin β15 or a unique fragment thereof, any suitable system can be used. The general nature of suitable vectors, expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Control sequences, such as recognition, promoter, operator, inducer, terminator and other sequences essential and/or useful in the regulation of expression, will be readily apparent to those skilled in the art, and may be associated with the natural thymosin β15 or with the vector used, or may be derived from any other source as suitable. The vectors may be modified or engineered in any suitable manner.

Correct preparation of nucleotide sequences may be confirmed, for example, by the method of Sanger et al. (*Proc. Natl. Acad. Sci.* U.S.A. 74:5463–7 (1977)).

A cDNA fragment encoding the thymosin β15 of the invention may readily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired thymosin β15 may be expressed. The extent of expression may be analyzed by SDS polyacrylamide gel electrophoresis-SDS-PAGE (Lemelli, *Nature* 227:680–685 (1970)).

Suitable methods for growing and transforming cultures etc. are usefully illustrated in, for example, Maniatis (Molecular Cloning, A Laboratory Notebook, Maniatis et al. (eds.), Cold Spring Harbor Labs, N.Y. (1989)).

Cultures useful for production of thymosin β15, or a peptide thereof, may suitably be cultures of any living cells, and may vary from prokaryotic expression systems up to eukaryotic expression systems. One preferred prokaryotic system is that of *E. coil,* owing to its ease of manipulation. However, it is also possible to use a higher system, such as a mammalian cell line, for expression of a eukaryotic protein. Currently preferred cell lines for transient expression are the HeLa and Cos cell lines. Other expression systems include the Chinese Hamster Ovary (CHO) cell line and the baculovirus system.

Other expression systems which may be employed include streptomycetes, for example, and yeasts, such as Saccharomyces spp., especially *S. cerevisiae*. Any system may be used as desired, generally depending on what is required by the operator. Suitable systems may also be used to amplify the genetic material, but it is generally convenient to use *E. coil* for this purpose when only proliferation of the DNA is required.

Standard detection techniques well known in the art for detecting RNA, DNA, proteins and peptides can readily be applied to detect thymosin β15 or its transcript to diagnose cancer, especially metastatic cancer or to confirm that a primary tumor has, or has not, reached a particular metastatic phase.

In one such technique, immunohistochemistry, anti-thymosin β15 antibodies may be used to detect thymosin β15 in a biopsy sample.

Anti-thymosin β15 antibodies may also be used for imaging purposes, for example, to detect tumor metastasis. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99m}$Tc), fluorescent labels, such as fluorescein and rhodamine, and biotin.

However, for in vivo imaging purposes, the position becomes more restrictive, as antibodies are not detectable, as such, from outside the body, and so must be labelled, or otherwise modified, to permit detection. Markers for this purpose may be any that do not substantially interfere with the antibody binding, but which allow external detection. Suitable markers may include those that may be detected by X-radiography, NMR or MIR. For X-radiographic techniques, suitable markers include any radioisotope that emits detectable radiation but that is not overtly harmful to the patient, such as barium or caesium, for example. Suitable markers for NMR and MIR generally include those with a detectable characteristic spin, such as deuterium, which may be incorporated into the antibody by suitable labelling of nutrients for the relevant hybridoma, for example.

In the case of in vivo imaging methods, an antibody or antibody fragment which has been labelled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the subject (such as a human) to be examined. The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99m. The labelled antibody or antibody fragment will then preferentially accumulate at the location of cells which contain thymosin β15. The labelled antibody or antibody fragment can then be detected using known techniques.

The antibodies may be raised against either a peptide of thymosin β15 or the whole molecule. Such a peptide may be presented together with a carrier protein, such as an KLH, to an animal system or, if it is long enough, say 25 amino acid residues, without a carrier. Preferred peptides include regions unique to thymosin β15, such as amino acid 7 to 12 of SEQ ID NO: 2, amino acid 21 to 24 of SEQ ID NO: 2 and amino acid 36 to 45 of SEQ ID NO: 2.

Polyclonal antibodies generated by the above technique may be used direct, or suitable antibody producing cells may be isolated from the animal and used to form a hybridoma by known means (Kohler and Milstein, Nature 256:795. (1975)). Selection of an appropriate hybridoma will also be apparent to those skilled in the art, and the resulting antibody may be used in a suitable assay to identify thymosin β15.

Antibodies, or their equivalents, may also be used in accordance with the present invention for the treatment or prophylaxis of cancers. Administration of a suitable dose of the antibody may serve to block production, or to block the effective activity of thymosin β15, and this may provide a crucial time window in which to treat the malignant growth.

Prophylaxis may be appropriate even at very early stages of the disease, as it is not known what actually leads to metastasis in any given case. Thus, administration of the antibodies, their equivalents, or factors which interfere with thymosin β15 activity, may be effected as soon as cancer is diagnosed, and treatment continued for as long as is necessary, preferably until the threat of the disease has been removed. Such treatment may also be used prophylactically in individuals at high risk for development of certain cancers, e.g., prostate.

A method of treatment involves attachment of a suitable toxin to the antibodies which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of suitable physiologically active compounds, which may be used, for example, to treat cancers.

It will be appreciated that antibodies for use in accordance with the present invention, whether for diagnostic or therapeutic applications, may be monoclonal or polyclonal as appropriate. Antibody equivalents of these may comprise: the Fab' fragments of the antibodies, such as Fab, Fab', F(ab')2 and Fv; idiotopes; or the results of allotope grafting (where the recognition region of an animal antibody is grafted into the appropriate region of a human antibody to avoid an immune response in the patient), for example. Single chain antibodies may also be used. Other suitable modifications and/or agents will be apparent to those skilled in the art.

Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad, Sci. U.S.A. 81,6851 (1985); Takeda et al., Nature 314,452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additonally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad Sci. U.S.A., 80, 7308–7312 (1983); Kozbor et al., Immunology Today, 4, 7279 (1983); Olsson et al., Meth. Enzymol., 92, 3–16 (1982)), and are preferably made according to the teachings of PCT Publication WO92/06193 or EP 0239400.

Humanized antibodies can be commercially produced by, for example, Scotgen Limited, 2 Holly Road, Twickenham, Middlesex, Great Britain.

Another method of generating specific antibodies, or antibody fragments, reactive against thymosin β15 is to screen phage expression libraries encoding immunoglobulin genes, or portions thereof, with a protein of the invention, or peptide fragment thereof. For example, complete Fab fragments, V H regions and V-region derivatives can be expressed in bacteria using phage expression libraries. See for example Ward, et al., *Nature* 341,544–546: (1989); Huse, et al., *Science* 246, 1275–1281 (1989); and McCafferty, et al., *Nature* 348, 552–554 (1990).

The antibody can be administered by a number of methods. One preferred method is set forth by Marasco and Haseltine in PCT WO94/02610, which is incorporated herein by reference. This method discloses the intracellular delivery of a gene encoding the antibody, in this case the thymosin β15 antibody. One would preferably use a gene encoding a single chain thymosin β15 antibody. The antibody would preferably contain a nuclear localization sequence, for example Pro-Lys-Lys-Lys-Arg-Lys-Val (SEQ ID NO:4) [Lawford, et al. Cell 46:575 (1986)]; Pro-Glu-Lys-Lys-Ile-Lys-Ser (SEQ ID NO:5) [Stanton, et al., *Proc. Natl. Acad. Sci. USA* 83:1772 (1986)], Gln-Pro-Lys-Lys-Pro (SEQ ID NO:6) [Harlow, et al., *Mol. Cell. Biol.* 5:1605 (1985)]; Arg-Lys-Lys-Arg (SEQ ID NO:7) for the nucleus. One preferably uses an SV40 nuclear localization signal. By this method one can intracellularly express a thymosin β15 antibody, which can block thymosin β15 functioning in desired cells.

In addition to using antibodies to inhibit thymosin β15, it may also be possible to use other forms of inhibitors. Inhibitors of thymosin β15 may manufactured, and these will generally correspond to the area of the substrate affected by the enzymatic activity. It is generally preferred that such inhibitors correspond to a frozen intermediate between the substrate and the cleavage products, but it is also possible to provide a sterically hindered version of the binding site, or a version of the binding site which will, itself, irreversibly bind to thymosin β15. Other suitable inhibitors will be apparent to the skilled person.

The invention also provides for the treatment of a cancer by altering the expression of the thymosin β15. This may be effected by interfering with thymosin β15 production, such as by directing specific antibodies against the protein, which antibodies may be further modified to achieve the desired result. It may also be possible to block the thymosin β15 receptor, something which may be more easily achieved by localization of the necessary binding agent, which may be an antibody or synthetic peptide, for example.

Affecting thymosin β15 gene expression may also be achieved more directly, such as by blocking of a site, such as the promoter, on the genomic DNA.

Where the present invention provides for the administration of, for example, antibodies to a patient, then this may be by any suitable route. If the tumor is still thought to be, or diagnosed as, localized, then an appropriate method of administration may be by injection direct to the site. Administration may also be by injection, including subcutaneous, intramusoular, intravenous and intradermal injections.

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients. Catheters are another preferred mode of administration.

Thymosin β15 expression may also be inhibited in vivo by the use of antisense technology. Antisense technology can be used to control gene expression through triple-helix formation or antisense DNA or RNA, both of which methods are based on binding of a polynucleotide to DNA or RNA. An antisense nucleic acid molecule which is complementary to a nucleic acid molecule encoding thymosin β15 can be designed based upon the isolated nucleic acid molecules encoding thymosin β15 provided by the invention. An antisense nucleic acid molecule can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NO: 1. A nucleic acid is designed which has a sequence complementary to a sequence of the coding or untranslated region of the shown nucleic acid. Alternatively, an antisense nucleic acid can be designed based upon sequences of a β15 gene, which can be identified by screening a genomic DNA library with an isolated nucleic acid of the invention. For example, the sequence of an important regulatory element can be determined by standard techniques and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1 (1)1986.

In addition, ribozymes can be used to inhibit in vitro expression of thymosin β15. For example, the nucleic acids of the invention can further be used to design ribozymes which are capable of cleaving a single-stranded nucleic acid encoding a β15 protein, such as a thymosin β15 mRNA transcript. A catalytic RNA (ribozyme) having ribonuclease activity can be designed which has specificity for an mRNA encoding thymosin β15 based upon the sequence of a nucleic acid of the invention (e.g., SEQ ID NO: 1 ). For example, a derivative of a Tetrahymena L-19 IVS RNA can be constructed in which the base sequence of the active site is complementary to the base sequence to be cleaved in a thymosin β15-encoding mRNA. See for example Cech, et al., U.S. Pat. No. 4,987,071; Cech, et al., U.S. Pat. No. 5,116,742. Alternatively, a nucleic acid of the invention could be used to select a catalytic RNA having a specific ribonuclease activity from a pool of RNA molecules. See for example Bartel, D. and Szostak, J. W. *Science* 261,1411–1418 (1993).

Methods for the diagnosis and prognosis of cancer using the polynucleotides and antibodies of the present invention are set forth in copending application (Docket No. 46403) Express Mail No. TB338582354US, the disclosure of which is herein incorporated by reference.

All references cited above or below are herein incoporated by reference.

The following Examples serve to illustrate the present invention, and are not intended to limit the invention in any manner.

EXAMPLES

METHODS

Cell Culture

The poorly metastatic AT2.1 subline and high metastatic AT3.1, AT6.1 and Mat lylu sublines derived from Dunning R3327 rat prostatic adenocarcinoma cells (provided by Dr. J. Issaacs, The Johns Hopkins University) were maintained in vitro in RPMI 1640 medium, supplemented with 10% fetal bovine serum (Hyclone Laboratories, Logan, Utah), 1% glutamine/penicillin/streptomycin (Irvine Scientific, Santa Ana, Calif.), and 250 nM dexamethasome (Sigma Chemical Co, St. Louis, Md.), under an atmosphere of 5% $CO_2$; 95% air at 37° C.

RNA Isolation and Northern Blot Analysis

Cells at 70% confluency were harvested and subjected to RNA isolation. Total RNA was prepared by acid guanidinium thiocyanate/phenol/chloroform extraction procedures. (Chomczynski, P. & Sacchi, *Anal. Biochem.* 167, 157–159 (1987)). Poly (A) RNAs were isolated from total RNA using Poly (A) Quik mRNA Isolation Kit (Stratagene, La Jolla, Calif.) or Micro Fast Track mRNA Isolation Kit (Invitrogen, San Diego, Calif.). 20 µg of total RNA or 2 µg of mRNA was size fractionated on a denaturing formaldehyde agarose gel (1.1%) and transferred onto Hybond-N$^+$ membrane (Amersham Corporation, Arlington Heights, Ill.) by capillary blotting in 0.05 M NaOH buffer according to the manufacturer's procedure. Northern blot filters were prehybridized for 3 hours at 42° C. in 5× Denhardt's, 50% formamide, 5× SSPE, 0.5% SDS solution containing 100 µg/ml denatured salmon sperm DNA (Stratagene), followed by overnight hybridization in fresh prehybridization solution with the addition of denatured probe labeled with [alpha-$^{32}$P] dCTP (New England Nuclear, Wilmington, Del.) using random primed DNA labeling kit (Boehringer Mannheim Biochemica, Indianapolis, Ind.). Filters were washed at increasing stringency to a final stringency of 0.2×SSC; 0.1% SDS at 55° C. Autoradiography was performed over two days at −80° C. using Kodak X-Omat's film with intensifying screen. For reprobing, the original probe was removed by the blots with boiling in 0.5% SDS water for 10 min.

mRNA differential display

DNase I digested 2 µg of total RNA from AT2.1, AT3.1 and AT6.1 cells grown to 70% confluency in RPMI 1640 medium supplemented with 10% fetal bovine serum and 250 nM dexamethasone were reverse-transcribed with 300 units of MMLV reverse transcriptase (Stratagene) in the presence of 2.5 µM of T 11 AG as primer and 20 µM dNTP for 60 min at 35° C. After heat inactivation of the reverse transcriptase at 95° C. for 5 min, 2 µl of the sample was amplified by PCR with T11 AG primer and arbitrary 10 mers in the presence of [α-$^{35}$]dATP (New England Nuclear). The PCR parameters were 94° C. for 30 sec, 42° C. for 1 min, and 72° C. for 30 sec for 40 cycles, followed by 5 min elongation at 72° C. PCR products were fractionated on a 6% polyacrylamide gel and visualized by autoradiography. Differentially expressed bands were cut out of the dried gels and reamplified by PCR using the corresponding sets of primers. The reamplified PCR fragments were used as probes for Northern blot analysis.

cDNA library screening

An oligo(dT)-primed cDNA library was constructed in the lambda gt10 vector (Amersham) using polyadenylated [poly (A)$^+$] RNA obtained from AT3.1 cells in culture. The library was screened with a $^{32}$P-labeled probe generated by PCR, using a 343 base pair AT3.1 cDNA isolated from differential display as template. Filters were hybridized with probe overnight at 65° C. in a 5× Denhardt's, 5× SSPE, 0.5% SDS solution containing 100 µg/ml denatured salmon sperm DNA, and washed at high stringency with 0.2×saline sodium citrate (SSC) and 0.1% SDS at 65° C. Inserts of positive clones were excised from λgt10 vector with EcoRI enzyme, subcloned into pbluescript II SK+/− (Stratagene) and sequenced using the Sequenase Version 2.0 sequencing kit (U.S. Biochemical, Cleveland, Ohio).

RT-PCR Analysis

Total RNA from each cell line was digested with RNase free DNase I (GIBCO BRL, Gaithersburg, Md.). DNase I digested 5 µg of total RNA was reverse transcribed using cDNA Cyling Kit (Invitrogen). The reverse transcrition mixture was purified with a Spin Column 300 (Pharmocia, Piscataway, N.J.). 10 µl of purified cDNA was amplified with primer sets of Tβ15 forward primer:

5'-TATCAGCTAGTGGCTGCACCCGCG-3' (SEQ ID NO:8) and reverse primer: 5'-AAATGCTGACCTTTCAGTCAGGGT-3' (SEQ ID NO:9); Tβ4 forward primer: 5'-ACTCTCAATTCCACCA TCTCCCAC-3' (SEQ ID NO:10), reverse primer: 5'-GCCTCTGAGCAGATCGTCTCTCCTTG-3' (SEQ ID NO:11); and Tβ10 forward primer:

5'-ATAATATCCCTGGGCAAACCGGTG-3' (SEQ ID NO:12), reverse primer: 5'-GAGTGGAG TACCTGGAGCGCGAGC-3' (SEQ ID NO:13), respectively. PCR amplification was performed in 50 µl of PCR reaction buffer (50 mM KCl, 10 mM Tris [pH 8.5], 1.5 mM $MgCl_2$) with 1 mM of dNTPs, 50 pmol of each primer, and 2.5 U of Taq polymerase (GIBCO BRL), overlaid with. 50 µl of mineral oil (Sigma). The PCR profile was 94° C., 30 sec; 60° C., 30 sec; and 72° C., 2 min for 30 cycles. Control studies of the RT-PCR were conducted using aliquats from the same samples and amplified with primers to the β-actin gene (Clontech, Palo Alto, Calif.). Amplification products were separated on 1.4% agarose gels.

In situ hybridization

Antisense and sense Tβ15 mRNA probes were prepared using Tβ15 cDNA inserted into the eukaryotic expression vector pcDNA3 (Invitrogen) as template and a digoxigenin RNA labeling kit (Boehringer Mannheim). Formalin-fixed paraffin-embedded sections were dewaxed, rehydrated, and digested with proteinase K (50 μg/ml) in 100 mM Tris, 50 mM EDTA buffer (pH 8) for 8 min at 37° C. Hybridization was performed in an automated instrument (Ventana Medical Systems, Tuscon, Ariz.) for 60 min at 42° C. with 10 pM digoxigenin-labeled riboprobe in 100 μl of hybridization buffer (50% deionized formamide, 4× SSC, 10% dextran sulfate, 1% SDS, and denatured herring sperm DNA (400 μg/ml)) per section under a liquid cover slip. The highest stringency of posthybridization washes was at 45° C. for 15 min in 0.1×SSC. Bound digoxigenin-labeled probe was detected by anti-digoxigenin alkaline phosphatase conjugate and visualized by nitroblue tetrazolium and 5-bromo-4-chloro-3-indolylphosphate (NBT-BCIP) color reaction. Sections were counterstained with nuclear fast red.

GST-Tβ fusion protein expression

PCR generated DNA fragments containing the full coding regions of Tβ15 and Tβ4 were ligated in frame into the BamHI-EcoRI site of the prokaryotic expression vector pGEX-2T (Pharmacia, Piscataway, N.J.). The pGEX-Tβ fusions were expressed in Escherichia coli, strain DH5α, by incubating with 0.1 mM isopropylthio-β-D-galactoside for 3 hours. Cells were recovered by centrifugation, washed, and suspended in phosphate buffered saline (PBS) containing 0.15 μ/ml aprotinin and 1 mM EDTA and lysed by sonication. After addition of Triton X-100 to a final concentration of 0.1% (v/v), intact cells and debris were removed by centrifugation. The supernatant was incubated with a 50% (v/v) slurry of glutathione-agarose (Pharmacia) in PBS. After the beads were washed with excess PBS and poured into a column, fusion proteins were eluted with a solution containing 50 mM Tris-HCl (pH 8.0) and 10 mM reduced glutathione (Sigma).

Actin binding experiment

Pyrene-labeled G-actin was prepared as previously described (Kouyama, et al., Eur. J. Biochem 114, 33–38 (1981). The final extents of polymerization were determined from the final levels of fluorescence of pyrene-labeled antin as previously described (Janmey, et al. Biochemistry 24, 3714–3723 (1985).

Transfection

Tβ15 cDNA was cloned into pcDNA3 in either the sense or antisense orientation relative to the constitutive human cytomegalovirus promoter and transfected into cells using lipofectin (GEBCO BRL, Gaithersburg, Md.). Individual stable transfectants were selected in media containing 600 μg/ml of G418 (GIBCO BRL). Control transfections were done with pcDNA3 DNA devoid of Tβ15.

Cell motility

Migration of transfectants was studied using a multiwell chamber assay as previously described (Kunda, et al., J. Cell Biol. 130, 725 (1995)) 48-well chemotaxis chambers were overlaid with 8-μm porosity polycarbonate filters (Nucleopore Corp., Pleasanton, Calif.) precoated with PBS containing 11.5 μg/ml fibronectin (Capple Organon Technica, Durham, N.C.). The migration of 5,000 cells placed in the upper well toward fetal bovine serum in the lower well was assayed following a 4 hour incubation at 37° C. After removal of cells from the upper side of the filters, cells that had passed through the filters and adhered to the lower side were fixed in formalin, washed with PBS and stained with Gill's triple strength hematoxylin (Polysciences, Warrington, Pa.) and counted under light microscopy.

Generation of polyclonal antibody 0.25 mg of a synthetic oligopeptide (IQQEKEYNQRS) representing the 11 carboxyl terminal amino acids of thymosin β15 dissolved in 380 ml of a 0.125M phosphate buffer, pH 7.4 was pipetted into reaction vessel containing 1.0 mg of keyhole limpet hemocyanin (Sigma). Then, 20 μl of 25% aqueous glutaraldehyde solution was added. After gentle agitation, first for 3 h at room temperature and then for 12 h at 4° C., the reaction mixture was diluted with 0.15M NaCl to a final concentration of 100 μg/ml. The diluted mixture was then used for immunization. New Zealand White rabbits were immunized with 30 μg of the C-terminal peptide of thymosin β15 as KLH conjugate emulsified with CFA. The first booster injection was given 6 weeks after the first immunization. Whereas subsequent booster injections were given at 3 weeks intervals. Production bleeds were obtained 2 weeks after the fifth boost. Antisera were affinity purified over the C-terminal peptide conjugated CNBr-activated Sepharose 4B column (Pharmacia) in 10 mM Tris-HCl, pH 7.4. After extensive washing of the column with 0.5M NaCl, 10 mM Tris, pH 7.4, the column was eluted with 0.2 M Glycine, 0.2 NaCl, pH 2.0. The purity and specificity of eluted fractions were examined by Western analysis.

Western analysis

GST-Tβ fusion proteins were run on a 12% SDS-polyacrylamide gel and transfered to a nitrocellulose membrane (0.2 mm, Schleicher & Schuell, Keene, N.H.). The blot was incubated with 5% nonfat dry milk in phosphate-buffered saline containing 0.1% Tween 20 (TBS-T) followed by incubation with the 1:1000 diluted affinity purified anti Tβ15 C-terminal peptide antibody for 1 h and washed 3 times with TBS-T. The blot was then incubated with horseradish peroxidase-conjugated anti-rabbit IgG antibody (Amersham Corp.) for 40 min, and a specific antibody reaction was detected by an enhanced chemiluminescence detection system (Amersham Corp.), Immunohistochemical staining Human prostate cancer sections were studied using an immunoperoxidase ABC kit (Vector, Burlingame, Calif.). Briefly, the 5 μm tissue sections were deparaffinized in xylene, rehydrated in graded alcohols, and blocked for endogenous peroxidase by 3% hydrogen peroxide (Sigma) in methanol for 30 min. The sections were treated with normal goat serum for 30 min and then incubated with an affinity purified anti Tβ15 C-terminal peptide antibody for 2 h at room temperature at 1:100 (v/v) dilution, followed by incubation with a biotinylated goat anti-rabbit IgG antibody for 30 min. After incubation with a preformed ABC complex for 30 min, specifically bound antibodies were visualized by using peroxidase substrate, 3, 3'-diaminobenzidine tetrahydrochioride (DAB). Sections were counterstained with Gill's hematoxylin.

RESULTS

Cloning of Tβ15

We compared patterns of gene expression by mRNA differential display analysis (Liang, P. & Pardee, A. B., Science 257, 967–971 (1992) in three variants of the Dunning rat tumor: the weakly metastatic, poorly motile line AT2.1 and the highly metastatic, highly motile lines AT3.1 and AT6.1. One band, which was detected in the more motile AT3.1 and AT6.1 lines by differential display (FIG. 1A) was confirmed by Northern (RNA) analysis to represent an overexpressed mRNA of approximately 420 nucleotides in AT3.1, AT6.1 as well as the related MatLyLu cell line but was not expressed in the poorly motile AT2.1 line (FIG. 1B). The gene was not expressed in other rat prostatic cell lines (non-metastatic) characterized by Northern analysis (data not shown).

To obtain a full-length complementary DNA (cDNA) clone of this gene, an AT3.1 cDNA library was screened using the originally cloned cDNA fragment from differential display as a probe. A positive clone with a 412 base pair insert was isolated, which contained a single open-reading frame encoding a 45 amino acid protein with a calculated molecular mass of 5304 (FIG. 2). The insert size of the clone was approximately the same as the molecular size of the transcript seen in Northern analysis suggesting that the clone contained the full length gene sequence. A computer assisted homology search against the Genebank and EMBL DNA databases revealed that the novel gene shared 49% nucleotide sequence homology with rat thymosins β4 and β10. Alignment of the deduced amino acid sequence of the cloned gene with members of the thymosin β family (Mihelic, M. & Voelter, Amino Acids 6, 1–13 (1994) showed 68% homology with thymosin β4, 62% with thymosin β10 and 60% with β9, β11 and β12 (FIG. 3). The results suggest that we have cloned a novel β thymosin, now named thymosin β15, from rat prostatic carcinoma cells.

Hydropathy analysis of the thymosin β15 protein sequence revealed no apparent membrane-spanning or membrane-associated regions and no amino-terminal signal sequence. The protein is highly hydrophilic with an estimated isoelectric point of 5.14 and contains regions common to all members of the thymosin β family. All β-thymosin family members previously studied, for example, have a putative actin binding region (LKKTET) 16 residues from the amino terminus (Vancompernolle, et al., EMBO J. 11, 4739–4746 (1992), Troys, et al., EMBO J. 15, 201–210 (1996). Thymosin β15 also has such a region, although the glutamic acid residue is replaced by an asparagine residue to form LKKTNT (FIG. 3). The principal region of nonconformity between members of the thymosin β family occurs at the carboxyl terminus and the thymosin β15 sequence as well shows no significant homology in this region with other family members.

Figure 11:
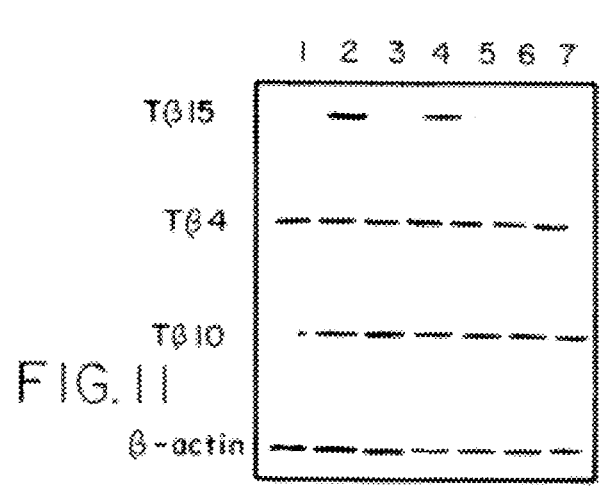
FIG. 11 is a 1.4% agarose gel electrophoresis of RT-PCR amplified β thymosins from the rat prostatic cell lines. Lane 1, weakly metastatic AT2.1; lane 2, 3 and 4, highly metastatic AT3.1, AT6.1 and Mat Lylu; lane 5 and 6, nonmetastatic NbE and MC2; lane 7, weakly metastatic Fb2. β-actin PCR was used as internal control of each sample.

Members of the β-thymosin family may be independently expressed in different tissues (Lin, et al., J. Biol. Chem. 266, 23347–23353 (1991), Voisin, et al. J. Neurochem. 64, 109–120 (1995). Although thymosin β15 is differentially expressed in the prostate carcinoma cell lines tested, all of these lines expressed equivalent levels of thymosins β4 and β10 by RT-PCR analysis (FIG. 11). The tissue distribution of thymosin β15 mRNA was examined in the major organs of the rat. No expression of thymosin β15 was detected in the heart, brain, lung, spleen, liver, skeletal muscle and kidney, whereas high expression was found in the testis (FIG. 4). Southern (DNA) analysis of Hind III-, EcoR I- and Pst I-restricted DNA from AT2.1 and AT3.1 cells with thymosin β15 cDNA probe revealed no gross structural alteration of the thymosin β15 gene in the tumor cells (data not shown). These results demonstrate that a novel member of the thymosin β family is upregulated in metastatic rat prostatic carcinoma cell lines, whereas expression of other thymosin β family members (β4 and β10) remains unchanged.

Cloning of Human Thymosin β15 by RT-PCR

DNase I digested 5 μg of total RNA from human prostatic carcinoma cell line PC-3 was reverse transcribed using cDNA Cycling Kit (Invitrogen). The reverse transcription mixture was purified with a Spin Column 300 (Pharmocia, Piscataway, N.Y.). 10 μl of purified cDNA reaction was amplified with primers F1 (5'-TATCAGCTAGTGGCTGCACCCGCG-3') (SEQ ID NO:8) and RI (5'-AAATGCT GACCTTTCAGTCAGGGT-3') (SEQ ID NO:9) designed to anneal to the outer ends of the thymosin β15 sequence. PCR amplification was performed in 50 μl of PCR reaction buffer (50 mM KCl, 10 mM Tris [pH 8.5], 1.5 mM MgCl$_2$) with 1 mM of dNTPs, 50 pmol of each primer, and 2.5 U of Taq polymerase (GIBCO BRL), overlaid with 50 μl of mineral oil (Sigma). The PCR profile was 94° C., 30 sec; 60° C., 30 sec; and 72° C., 2 min for 30 cycles. Control studies of the RT-PCR were conducted using aliquats from the same samples and amplified with primers to the β-actin gene (Clontech, Palo Alto, Calif.). Amplification products were separated on 1.6% agarose gels. The amplified PCR product was ligated to pCR using TA cloning kit (Invitrogen, San Diego, (Calif.), and then DNA sequenced. The sequence of the PCR product of human prostatic carcinoma cells amplified by the thymosin β15 primers was surprisingly 100% identical to the thymosin β15 sequence obtained from the rat prostatic carcinoma cells.

Expression of Tβ15 mRNA in human prostate cancer

Figure 5B:
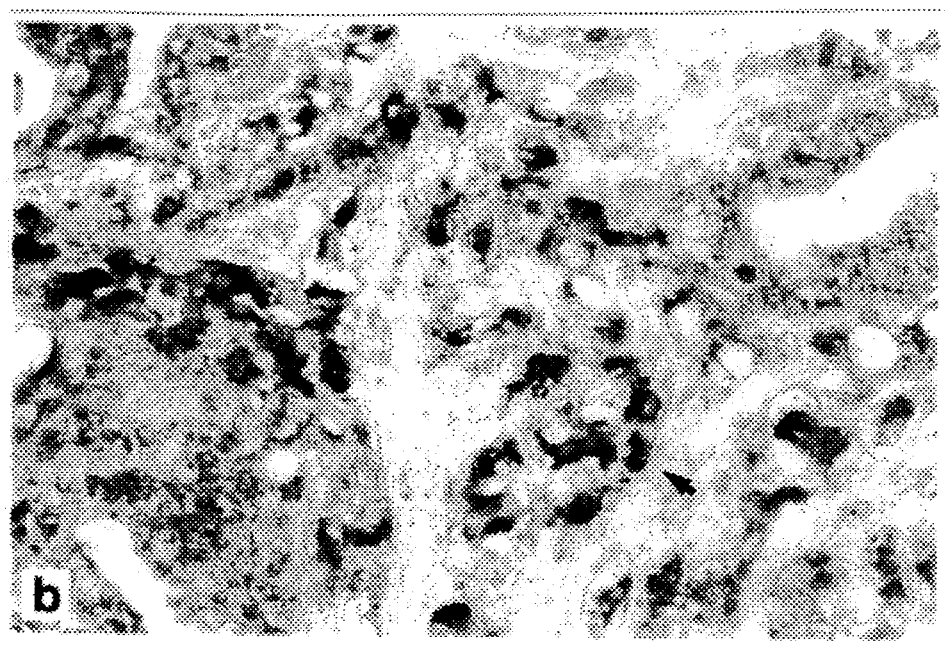

To determine whether this thymosin family member may be expressed in human prostate cancer, we examined human prostatic carcinoma cell line PC-3 by RT-PCR with forward and reverse primers for thymosin β15. The PC-3 cells showed a low level of thymosin β15 expression. The DNA sequence of the amplified PCR product was 100% identical to the rat thymosin β15 sequence. We conducted in situ hybridization study on samples from patients with varying grades of prostatic carcinomas using a thymosin β15 probe. The tissue sections allowed direct comparison of normal and malignant elements on the same samples. The stromal elements within and around the tumor cell masses, as well as the nonmalignant prostatic epithelium adjacent to the tumor showed little background hybridization with the thymosin β15 antisense probe. In contrast, specific tumor cell islands exhibited a strong specific thymosin β15 signal when probed with antisense (FIG. 5A, small arrow) but not with a sense RNA probe (data not shown). Although nearly all of the tumor cells in the positive islands expressed thymosin β15 mRNA, not all patient specimens were positive and not all islands in a single prostate were positive (FIG. 5A, large arrow). The majority of the negative tumor cells were in non-invasive in situ carcinomas whereas highly invasive tumors were consistently positive (FIG. 5B). Thus a novel β thymosin, first detected in metastatic rat prostate carcinoma cell lines, is upregulated in human prostate cancer.

Effect of Tβ15 on on actin polymerization

Figure 6A:
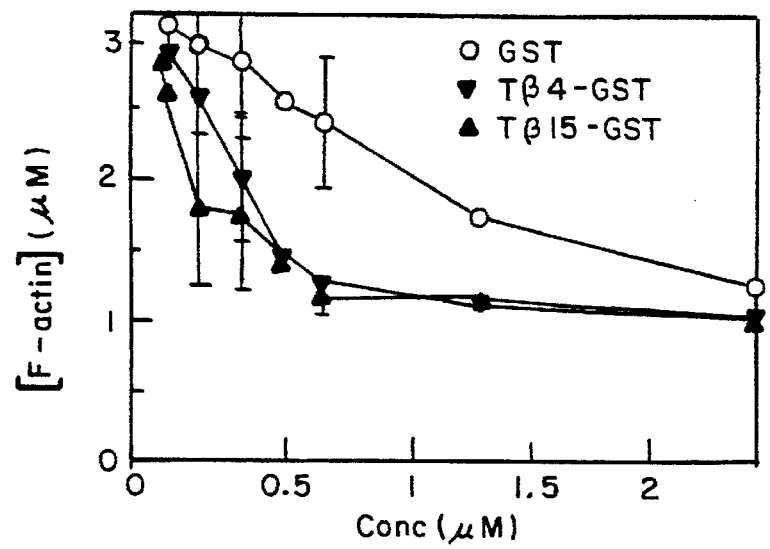
FIGS. 6A, 6B and 6C show the effect of Tβ15 on actin polymerization.
Figure 6B:
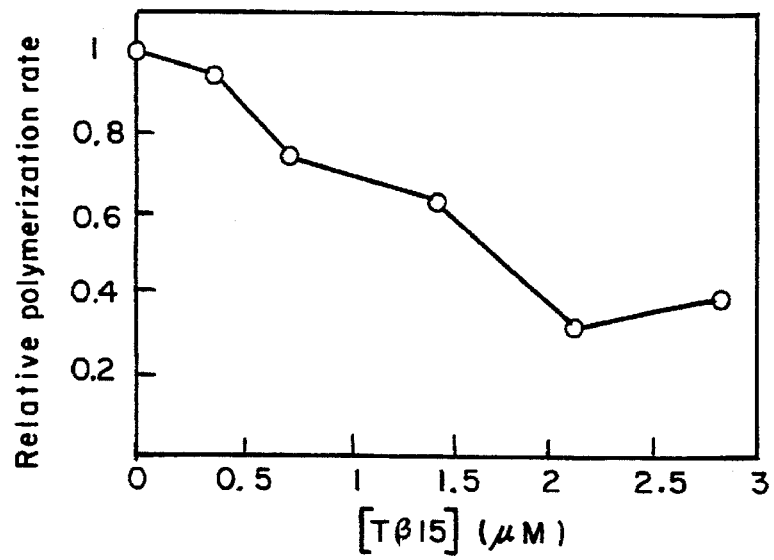
Figure 6C:
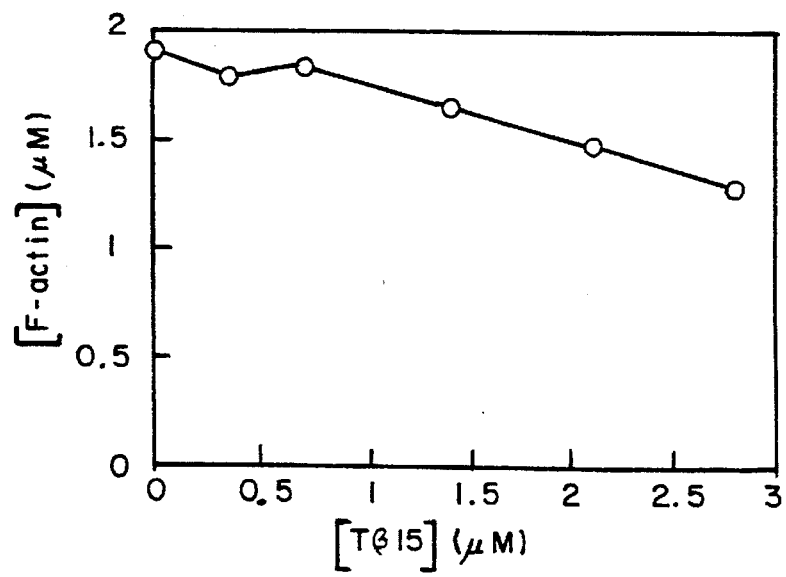

Because thymosin β15 retains a putative actin-binding domain, we tested its effect on actin polymerization using recombinant fusion proteins. The results, shown in FIG. 6A, reveal that a glutathione-S-transferase (GST)/thymosin β15 fusion protein inhibits polymerization of pyrene-derivatized actin monomers to an equal or slightly greater extent than a GST/thymosin b4 fusion protein, suggesting that these two proteins have similar actin-sequestering properties. Similar results were obtained when thymosin β15 was cleaved from the GST-fusion protein with thrombin and subsequently analyzed for its ability to inhibit the rate and extent of actin polymerization (FIG. 6B and C). The difference in apparent affinity for actin between free and GST-fused thymosin β15 is likely related to the GST-mediated dimerization of the fusion peptides to form complexes with two actin monomer binding sites that either bind actin more tightly or bind to the end of the growing filament, thereby inhibiting polymerization at low molar ratios to total actin. One example of such an effect is the strong retardation of actin assembly by actobindin, which appears to function as a dimer of thymosin-like actin binding sites (Bubb, et al., Biochemistry 34, 3921–3926 (1995).

Effect of Tβ15 on cell motility

Figure 7A:
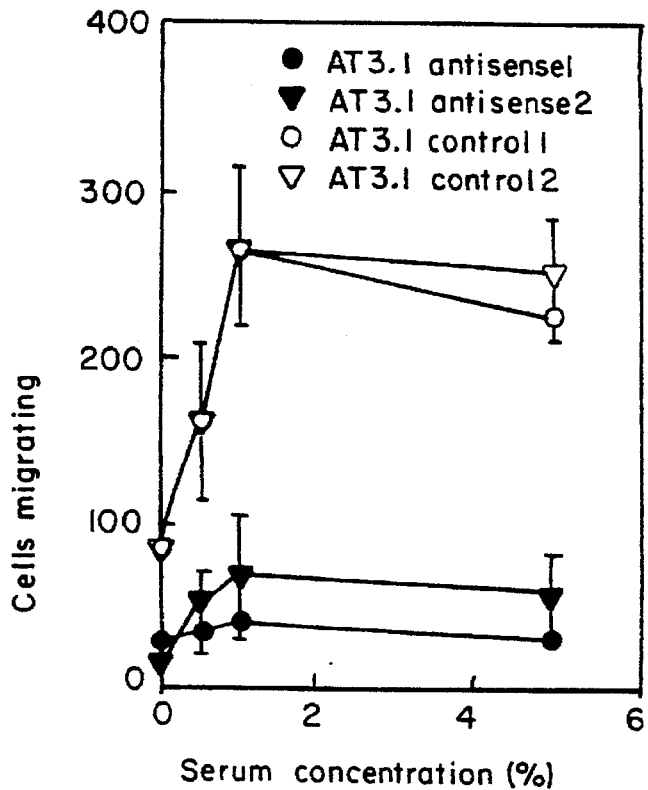
FIGS. 7A, 7B and 7C show serum stimulated migration of control transfected and Tβ15 transfected Dunning R-3327 variants and their growth rate.
Figure 7B:
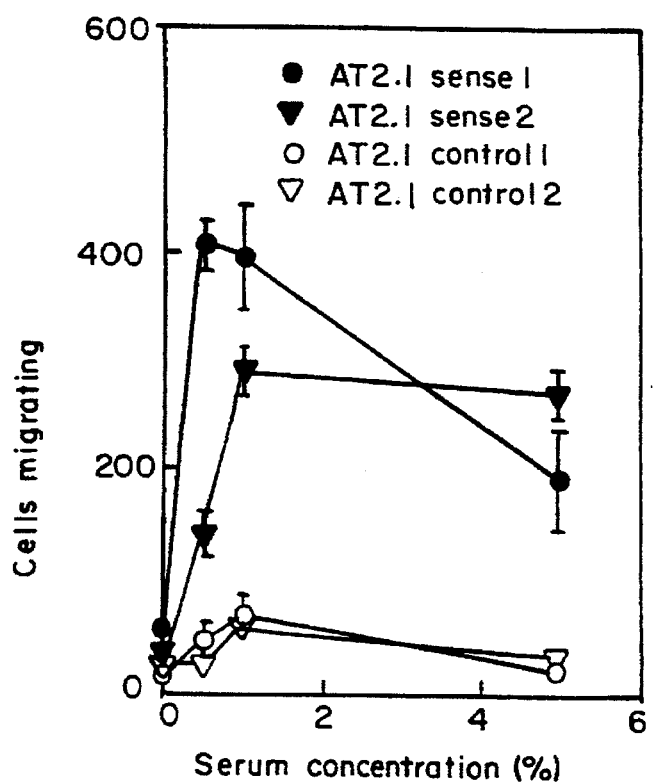
Figure 7C:
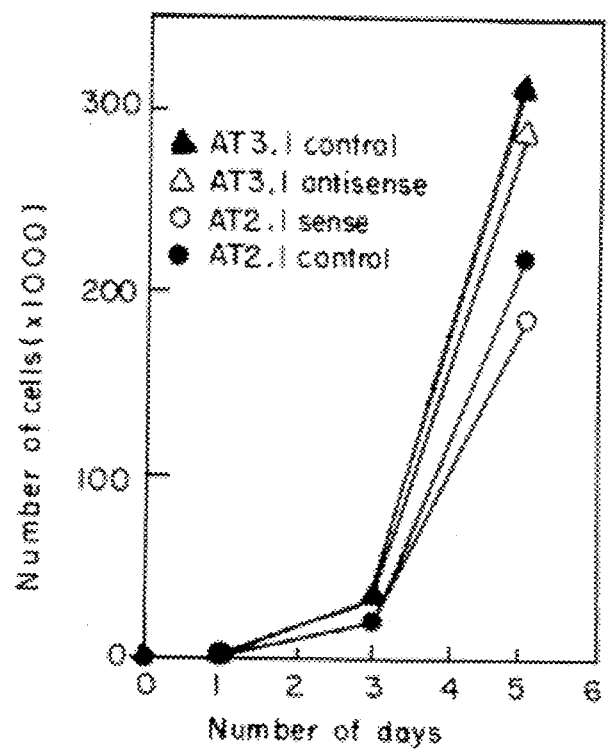

To determine whether thymosin β15 expression had an effect on cell motility, we transfected highly motile AT3.1 cells with a eukaryotic expression vector (pcDNA3) containing the thymosin β15 gene in antisense orientation driven by the constitutive human cytomegalovirus promoter. The transfected cells growing in selective (G418) media were examined for expression of antisense transcripts of the thymosin β15 gene by strand-specific polymerase chain reaction (PCR) amplification (Zhou, et al., *Cancer Res.* 52, 4280–4285 (1992). Analysis of cell motility in a multiwell Boyden chamber apparatus (Boyden, S. V., *J. Exp. Med.* 115, 453–466 (1962)) using fetal bovine serum as a migration stimulus revealed that the motility of the transfectants which showed expression of antisense transcripts was significantly reduced relative to the vector-only controls (FIG. 7A). Two antisense transfected clones which did not express antisense transcripts failed to show any decreased rate of cell motility (data not shown). In a further experiment, poorly motile AT2.1 cells, transfected with sense thymosin β15 constructs and confirmed to express thymosin β15 by Northern analysis, were shown to have significantly increased stimulated motility relative to their vector controls (FIG. 7B). Both the sense and antisense thymosin β15 transfectants showed similar rates of cell proliferation relative to controls suggesting differential specificity for different cellular events (FIG. 7C). The results demonstrate that thymosin β15, which is upregulated in the highly motile AT3.1 and AT6.1 Dunning tumor cell lines, is a positive regulator of cell motility which is an important component of cancer metastasis.

Immunohistochemical detection of Tβ15 in prostate carcinoma

Figure 8A:
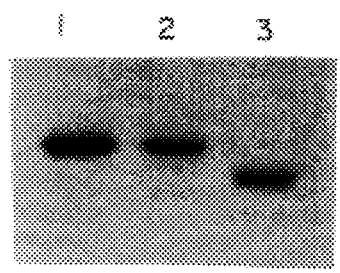
FIGS. 8A and 8B show Western analysis of thymosin β-GST fusion protein.
Figure 8B:
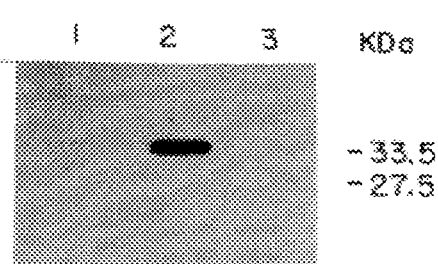

A polyclonal antibody was raised against a peptide representing the 11 C-terminal amino acids of thymosin β15. Synthesized peptide was coupled with a carrier, keyhole limpet hemocyanin (KLH), and injected into rabbits. Antiserum was affinity-purified over the C-terminal peptide coupled CNBr-activated sepharose 4B column. To test the specificity of the purified antibody, we performed Western analysis of the GST/thymosin β fusion proteins with the affinity-purified anti C-terminal antibody. The purified antibody strongly reacted with GST-thymosin β15 fusion protein, but did not cross react with GST-thymosin β4, and not with GST alone (FIG. 8) showing its specificity.

Figures 10A, 10B, 10C, 10D:
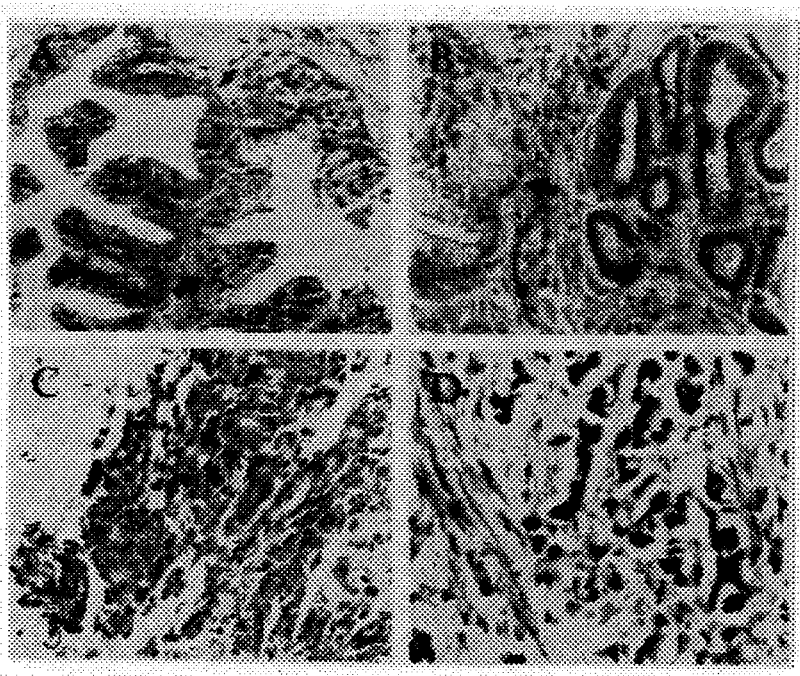
FIG. 10A, 10B, 10C and 10D show immunohistochemical staining of human prostatic carcinoma tissues with an affinity purified polyclonal antibody to thymosin β15. A. Non-malignant prostatic epithelia (large arrow) and high-grade prostatic intraepithelial neoplasia (PIN) (small arrow). B. Moderately differentiated prostatic carcinoma showing heterogeneoue immunostaining (small arrow, positive; large arrow, negative). C. Poorly differentiated prostatic carcinoma. D. Single cells invading stroma showing intense staining.

We used the affinity purified polyclonal thymosin β15 antibody for immunohistochemical study of human prostate carcinoma. The results are summarized below in Table 1. The thymosin β15 immunostaining was observed in the cytoplasms of epithelial cells in neoplastic prostates but not in normal prostates and not in the stromal cells (FIG. 10A, large arrow). Among the investigated malignant epithelia, the poorly differentiated prostate carcinomas displayed the most extensive and intense thymosin β15 immunoreaction (FIG. 10C), followed by moderately differentiated prostate carcinomas in which not all carcinomas expressed thymosin β15 showing partial positivity (FIG. 10B). In some cases, high-grade prostatic intraepithelial neoplasia (PIN) showed thymosin β15 immunostaining, but to a lesser extent FIG. 10A, small arrow). In poorly differentiated invasive carcinoma, single cells invading stroma displayed intense staining (FIG. 10D). The expression of thymosin β15 well correlated with Gleason grade of prostate carcinoma.

TABLE 1

THYMOSIN β15 EXPRESSION IN HUMAN PROSTATE CARCINOMA

| Prostate | No. | Negative[a] | Partial[b] | Positive[c] |
| --- | --- | --- | --- | --- |
| BPH | 2 | 2 | 0 | 0 |
| Ca Gleason 2–5 | 5 | 3 | 2 | 0 |
| Ca Gleason 6–8 | 25 | 4 | 7 | 14 |
| Ca Gleason 9–10 | 6 | 0 | 1 | 5 |
| Ca (with met) | 3 | 0 | 1 | 2 |

Figure 9:
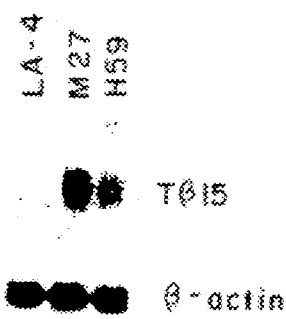
FIG. 9 shows a Northern analysis of thymosin β15 in mouse lung tumor cells. LA-4: mouse lung adenoma cell line; M27 and H59: metastatic variants derived from mouse Lewis lung adenocarcinoma cell line, Northern blot analysis revealed that the probe detected the thymosin β15 mRNA expression in M27 cells, less expression in H59 cells, but no expression in LA-4 cells.

(BPH - Benign Prostate Hyperplasia; Ca - Carcinoma)
[a] less than 10% cells showing positivity
[b] heterogeneous staining with 30–75% of cells showing postitivity
[c] homogeneous staining with 75–100% of cells showing positivity Expression of thymosin β15 mRNA in mouse lung carcinoma To determine whether thymosin β15 may be expressed in other kind of cancer cells, we tested mouse lung carcinoma cell lines by Northern analysis. The results showed the thymosin β15 expression in metastatic cell lines M27 and H59, but showed no expression in a nonmetastatic cell line LA-4 (FIG. 9).

DISCUSSION

Progression to the metastatic stage is directly correlated with mortality from prostatic carcinoma. It therefore follows that the early diagnosis, prevention, or therapeutic treatment of metastatic progression would lead to more effective control of this disease. The Dunning R-3327 rat prostatic adenocarcinoma model provides several sublines with varying metastatic ability, all of which derive from an original spontaneous tumor and which provide an opportunity to study the steps leading to prostate cancer metastases (Mohler, *Cancer Metast. Rev.* 12, 53–67 1993) and Pienta, et al. *Cancer Surveys* 11, 255–263 (1993)). By comparing gene expression among the Dunning cells, we cloned a novel member of the thymosin β family, thymosin β15, which is expressed in highly metastatic prostate cancer cells but not in non- or weakly metastatic cells. The related family members thymosin β4 and β10 are expressed equally in all of the cell lines tested such that their expression does not vary with increasing metastatic potential.

Thymosin β15 binds G-actin and retards actin polymerization. Because the highly motile prostate cancer cell lines showed high level expression of thymosin β15, we tested whether thymosin β15 transfection into the Dunning rat carcinoma cell lines could influence cell motility. Our results show clearly that transfection of sense or antisense thymosin β15 constructs into rat prostatic carcinoma cells can significantly modulate stimulated cell migration, a property not previously associated with β-thymosins. In cancer, the enhanced movement of malignant tumor cells through connective tissues is a major contributor to progression toward the metastatic stage. In order to metastasize, a tumor cell must initially dissociate from the primary tumor, migrate through connective tissue and capillary walls into the circulatory system, and migrate again across the vascular wall into a secondary site. Therefore, increases in thymosin β15 expression in malignant prostate carcinoma cells are believed to mediate an important change in tumor progression toward metastasis and that the expression of thymosin β15 is a useful marker for diagnosis and prognosis of cancer malignancy.

Cell motility is typically associated with coordinated disassembly and reformation of the cortical actin network (Cunningham, et al., *Science* 251, 1233–1236 (1991), Haugwitz, et al., *Cell* 79, 303–314 (1994) and Stossel, Science 260, 1086–1094 (1993)). Enhanced expression or activation of thymosin's actin binding function may therefore stimulate motility by enhancing the depolymerization phase of this process. The finding that a molecule which acts to retard actin polymerization may stimulate cell motility is consistent with the recent finding of Hug et al. (Hug, et al., Cell 81, 591–600 (1995) which showed that over expression of an action capping protein in Dictyostelium cells led to an increased rate of cell motility. The findings on the relationship between actin depolymenzation and increased motility also support our hypothesis that the upregulation of thymosin β15 may represent an important step in the progression of prostatic carcinoma to the metastatic state. The finding that thymosin β15, which is upregulated in more highly metastatic rat prostate cancer cell lines, is also upregulated in human prostate cancer is intriguing. At present, the best markers for prostate cancer, such as PSA expression, are most useful for early detection of prostate cancer. However, they do not allow any distinction of metastatic tumor from non-metastatic tumors.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. An isolated polynucleotide encoding human thymosin β15 comprising the amino acid sequence as set forth in SEQ ID NO:2.

2. An isolated polynucleotide encoding a polypeptide comprising a peptide having amino acid sequence 36 to 45 of SEQ ID NO: 2.

3. The polynucleotide of claims 1 or 2 wherein the polynucleotide is DNA.

4. The polynucleotide of claims 1 or 2 wherein the polynucleotide is cDNA.

5. The polynucleotide of claims 1 or 2 wherein the polynucleotide is RNA.

6. An isolated polynucleotide having the nucleotide sequence of SEQ ID NO:1, or the complement thereto.

7. An isolated polynucleotide encoding human thymosin β15 having the nucleotide sequence of nucleotides 98–232 of SEQ ID NO:1, or the complement thereto.

8. A recombinant vector containing the DNA of claim 6 or 7.

9. A host cell containing the vector of claim 8.

10. An isolated nucleotide segment which comprises 30 to 50 nucleotides and hybridizes under stringent conditions to a DNA fragment having the nucleotide sequence set forth in SEQ ID NO: 1.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
  ( A ) LENGTH: 412 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
  ( A ) NAME/KEY: Coding Sequence
  ( B ) LOCATION: 98...232
  ( D ) OTHER INFORMATION: Exon 1

( x i ) SEQUENCE DESCRIPTION: SEQ ID NO:1:

```
TATCAGCTAG TGGCTGCACC CGCGAACACC ACCCTGGTCC GGAGTAGCTG CGGACAGAAT        60

TGCTGGCCTA GTAGAAGCTT TGGAACGAGC AGTCAAG ATG AGT GAT AAA CCA GAC       115
                                        Met Ser Asp Lys Pro Asp
                                         1               5

TTA TCA GAA GTT GAA ACA TTT GAC AAA TCA AAG TTG AAG AAG ACT AAT        163
Leu Ser Glu Val Glu Thr Phe Asp Lys Ser Lys Leu Lys Lys Thr Asn
         10              15                  20

ACT GAA GAA AAG AAT ACT CTT CCT TCG AAG GAA ACT ATC CAG CAG GAG        211
Thr Glu Glu Lys Asn Thr Leu Pro Ser Lys Glu Thr Ile Gln Gln Glu
         25              30                  35

AAA GAA TAT AAT CAA AGA TC ATAAATGAG ATTCTCCTCT CAAGAGCAAC TTCAAC      267
Lys Glu Tyr Asn Gln Arg Ser
 40                      45

TTTGCTGGAT AGTCTTGGAT TTAGACATGT TTCTGTAAAC CTATCCAATA TGTAGACATT      327

TTAGGCGGTT CCTGATAGGT TCTTAAGTAC CCTGACTGAA AGGTCAGCAT TTAACACCAA      387

TCATTAAATG TGTTTCCAC TGCTC                                             412
```

( 2 ) INFORMATION FOR SEQ ID NO:2:

( i ) SEQUENCE CHARACTERISTICS:
  ( A ) LENGTH: 45 amino acids
  ( B ) TYPE: amino acid ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

| Met | Ser | Asp | Lys | Pro | Asp | Leu | Ser | Glu | Val | Glu | Thr | Phe | Asp | Lys | Ser |
|---|---|---|---|---|---|---|---|---|---|---|---|---|---|---|---|
| 1 | | | | 5 | | | | | 10 | | | | | 15 | |
| Lys | Leu | Lys | Lys | Thr | Asn | Thr | Glu | Glu | Lys | Asn | Thr | Leu | Pro | Ser | Lys |
| | | | 20 | | | | | 25 | | | | | 30 | | |
| Glu | Thr | Ile | Gln | Gln | Glu | Lys | Glu | Tyr | Asn | Gln | Arg | Ser | | | |
| | | | 35 | | | | | 40 | | | | 45 | | | |

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

AGGGAACGAG                                                                                                    10

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:4:

| Pro | Lys | Lys | Lys | Arg | Lys | Val |
|---|---|---|---|---|---|---|
| 1 | | | | 5 | | |

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:5:

Pro Glu Lys Lys Ile Lys Ser
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:6:

Gln Pro Lys Lys Pro
1               5

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (v i) ORIGINAL SOURCE:

(x i) SEQUENCE DESCRIPTION: SEQ ID NO:7:

Arg Lys Lys Arg
1

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

-continued (vi) ORIGINAL SOURCE:

(xi) SEQUENCE DESCRIPTION: SEQ ID NO:8:

TATCAGCTAG TGGCTGCACC CGCG                                                                                  24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

AAATGCTGAC CTTTCAGTCA GGGT                                                                                  24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

ACTCTCAATT CCACCATCTC CCAC                                                                                  24

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

GCCTCTGAGC AGATCGTCTC TCCTTG                                                                                26

(2) INFORMATION FOR SEQ ID NO:12:

(i) SEQUENCE CHARACTERISTICS:
        (A) LENGTH: 24 base pairs ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:12:

ATAATATCCC TGGGCAAACC GGTG                                                                              2 4

( 2 ) INFORMATION FOR SEQ ID NO:13:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

GAGTGGAGTA CCTGGAGCGC GAGC                                                                              2 4